(12) United States Patent
Desai et al.

(10) Patent No.: US 8,063,251 B2
(45) Date of Patent: Nov. 22, 2011

(54) PROCESS FOR THE PREPARATION OF OPTICALLY PURE R (−) SALBUTAMOL AND ITS PHARMACEUTICALLY ACCEPTABLE SALTS

(75) Inventors: Parimal Hasmukh Desai, Mumbai (IN); Narendra Jagannath Salvi, Mumbai (IN); Bharatkumar Surendra Patravale, Mumbai (IN); Subramanian Seetharaman, Mumbai (IN); Dilip Jibhau Patil, Mumbai (IN); Khandu Shankar Ghogare, Mumbai (IN)

(73) Assignee: Aarti Healthcare Limited, Mumbai (IN)

( * ) Notice: Subject to any disclaimer, the term of this patent is extended or adjusted under 35 U.S.C. 154(b) by 0 days.

(21) Appl. No.: 12/374,318

(22) PCT Filed: Sep. 25, 2006

(86) PCT No.: PCT/IN2006/000391
§ 371 (c)(1),
(2), (4) Date: Mar. 2, 2010

(87) PCT Pub. No.: WO2008/015689
PCT Pub. Date: Feb. 7, 2008

(65) Prior Publication Data
US 2010/0204516 A1    Aug. 12, 2010

(30) Foreign Application Priority Data
Aug. 2, 2006   (IN) .......................... 1221/MUM/2006

(51) Int. Cl.
*C07C 209/88* (2006.01)
*C07B 57/00* (2006.01)
(52) U.S. Cl. .................... 564/425; 564/304; 564/438
(58) Field of Classification Search ............... 564/304
See application file for complete search history.

(56) References Cited

U.S. PATENT DOCUMENTS

| | | | |
|---|---|---|---|
| 5,399,765 A | 3/1995 | Gao et al. | |
| 5,442,118 A | 8/1995 | Gao et al. | |
| 6,365,756 B1 | 4/2002 | Stevens et al. | |
| 6,995,286 B2 * | 2/2006 | Hamied et al. | 564/365 |
| 7,049,469 B2 | 5/2006 | Kreye et al. | |

FOREIGN PATENT DOCUMENTS

| | | |
|---|---|---|
| WO | 0248090 | 6/2002 |
| WO | 2005113481 | 12/2005 |

OTHER PUBLICATIONS

Database CAPLUS on STN, Acc. No. 1986:460405, Kimoto, JP 61007238 A (Jan. 13, 1986) (abstract).*
International Search Report in PCT/IN2006/000391, date mailed May 3, 2007.
Hartley et al., Journal of Medicinal Chemistry, vol. 14, 895-896, date printed on reference Mar. 2, 1971.

* cited by examiner

*Primary Examiner* — Brian J Davis

(57) ABSTRACT

A process for the preparation of optically pure R (−) salbutamol of formula (6) and its pharmaceutically acceptable salts by using a (+) 4-nitro tartranilic acid as the resolving agent and a binary solvent system comprising alkyl acetate and $C_1$ to $C_4$ branched or normal chain alcohol for dissolution of the racemic mixture and resolving agent and purification of the 4-nitro tartranilic acid salt of R (−) salbutamol. 4-nitro tartranilic acid salt of R (−) salbutamol is converted into formic acid salt of R (−) 4-benzyl salbutamol followed by basification and debenzylation to form optically pure R (−) salbutamol. Optically pure (R)-salbutamol is obtained in good yield and high purity. The optically pure R (−) salbutamol is optionally converted into pharmaceutically acceptable salts.

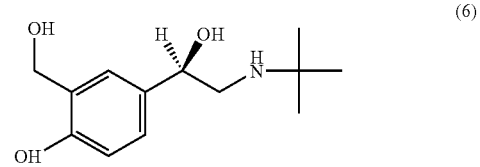

(6)

14 Claims, No Drawings

PROCESS FOR THE PREPARATION OF OPTICALLY PURE R (−) SALBUTAMOL AND ITS PHARMACEUTICALLY ACCEPTABLE SALTS

CROSS-REFERENCES TO RELATED APPLICATIONS

This present application is a U.S. national phase application of the international application PCT/IN2006/000391, entitled "A PROCESS FOR THE PREPARATION OF OPTICALLY PURE R (−) SALBUTAMOL AND ITS PHARMACEUTICALLY ACCEPTABLE SALTS", filed on Sep. 25, 2006, which in turn claims priority to the Indian patent application 1221/MUM/2006 similarly entitled and filed on Aug. 2, 2006, each of which is herein incorporated by reference.

TECHNICAL FIELD OF THE INVENTION

This invention relates to a process for the preparation of optically pure R-(−)-salbutamol and its pharmaceutically acceptable salts.

Salbutamol is also known as Albuterol. The chemical name of Salbutamol is 2-(N-t-butylamino)-1-(4-hydroxy-3-hydroxymethylphenyl)ethanol. Salbutamol is a short-acting beta.sub.2-adrenergic receptor agent used for the relief of bronchospasm in conditions such as asthma and Chronic obstructive pulmonary disease (COPD). Salbutamol is commonly available as a racemate. R-isomer of salbutamol is reported to be more potent, approximately 80 times more potent, than its S-isomer.

BACKGROUND OF THE INVENTION

Hartley et al (Journal of Medicinal Chemistry, Vol. 14, 895-896) discloses a method for resolution of salbutamol precursor by using tartaric acid derivatives such as di p-toluoyl tartaric acid.

U.S. Pat. No. 5,399,765 discloses a process for the preparation of optically pure (R)- and (S)-isomers by the resolution of a mixture of enantiomers of albuterol precursor, methyl 5-[2-[(1,1-dimethylethyl)amino]-1-hydroxyethyl]-2-hydroxy benzoate using a chiral acid as the resolving agent. The chiral acid is selected from the group consisting of (−) di-toluoyl-L-tartaric acid and (+)-di-toluoyl-D-tartaric acid. The process results into diastereomeric salt having 80-99% enantiomeric excess (e e) of desired enantiomers of albuterol, which on treatment with base liberates desired enantiomers of albuterol. The process is not cost-effective as the yield of optically pure R- and S-isomer is in the range of 21-43%.

U.S. Pat. No. 5,442,118 disclose a process for the preparation of optically pure (R)- and (S)-isomers of albuterol and similar ethanol amines by the asymmetric reduction of iminoketones with borane as reducing agent, such as borane-dimethyl sulfide or borane-tetrahydrofuran, in the presence of a chiral 1,3,2-oxazaborole catalyst. The process uses costly reagents and gives low optical purity of the order of 93-95% ee.

U.S. Pat. No. 6,365,756 discloses a process for the production of optically enriched (R)- or (S)-albuterol by first preparing a novel ketal derivative of albuterol, namely 2-(N-t-butylamino)-1-(+2,2-dimethyl-1,2-benzodioxin-6-yl)ethanol. The resolution is carried out with a chiral tartaric acid derivative such as (+) or (−) di-O-benzoyl tartaric acid or di-toluoyl tartaric acid. The process is a complicated multistage process involving resolution of the ketal derivative. The process also results into low enantiomeric excess of the order of 65% (based on the values given in the examples) and reduces its economic viability. This process also requires additional crystallization thereby lowering the overall yield.

WO2002/048090 discloses a process for the preparation of optically pure (R)- and/or (S)-salbutamol by resolving a racemic or optically impure mixture of enantiomers of salbutamol or its precursor by using chiral acid, (L)- or (D)-tartaric acid. The process results into good enantiomeric excess. The resolving agent is not recovered and reused. The undesired (S)-isomer salbutamol is also not converted into desired (R)-isomer.

WO2005/113481 discloses a process for the preparation of (R)-Salbutamol. A mixture of racemic salbutamol is treated with D-di-benzoyl tartaric acid, in the ratio of 1:0.5 to 1.3 mol and in the presence of $C_1$ to $C_4$ alcohol to obtain (R)-Salbutamol.D-di-benzoyl tartaric acid. The crude product is crystallized by seeding with (R) Salbutamol. D-di-benzoyl tartaric acid. The product is further recrystallized in methanol. The process results into high enantiomeric excess but low overall yield (based on the values given in the examples) and is not therefore, economically viable.

U.S. Pat. No. 7,049,469 discloses a process for preparing (R)-salbutamol. The process comprises of asymmetric hydrogenation of prochiral salbutamone in the presence of Rhodium and a chiral bidentate phosphine ligand as catalyst system. The process utilizes very costly catalyst and results into low enantiomeric excess. Costly reagent and low enantiomeric excess reduce the feasibility of the process on industrial scale Most of the prior art processes in general do not recover and reuse the resolving agent, thereby rendering them costly. Despite the many attempts of the prior art to prepare optically pure salbutamol, there is still need to develop processes, which are cost-effective without sacrificing the optical purity of Salbutamol.

SUMMARY OF THE INVENTION

An object of the invention is to provide an efficient and cost-effective process for the preparation of highly optically pure (R)-salbutamol in high yield by the resolution of a racemic mixture of salbutamol precursor with a (+) 4-nitro tartranilic acid as a resolving agent in the presence of a binary solvent system consist of alkyl acetate and $C_1$ to $C_4$ branched or normal chain alcohol with the simultaneous recovery of the (+) 4-nitro tartranilic acid.

Another object of the invention is to provide an efficient and cost-effective process for the preparation of highly optically pure (R)-salbutamol in high yield by the resolution of a racemic mixture of salbutamol precursor with a (+) 4-nitro tartranilic acid as a resolving agent in the presence of a binary solvent system consist of alkyl acetate and $C_1$ to $C_4$ branched or normal chain alcohol with the simultaneous recovery of undesired (S)-isomer of salbutamol and traces (R)-isomer and racemization thereof to racemic mixture of 4-benzyl salbutamol for use in the process of the invention so as to minimize wastage of the reactants.

DETAILED DESCRIPTION OF THE INVENTION

According to the invention there is provided a process for the preparation of optically pure R (−) salbutamol of formula (6):

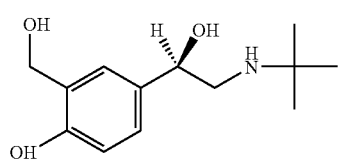

Formula 6 and its pharmaceutically acceptable salts, the process comprising
a) dissolving a racemic mixture of 4-benzyl salbutamol (salbutamol precursor) of the formula (1):

Formula 1

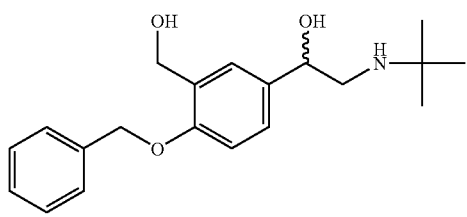

and (+) 4-nitro tartranilic acid of the formula (2):

Formula 2

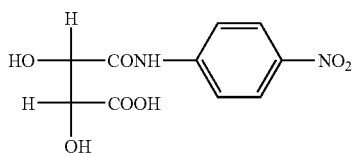

in a binary solvent system comprising alkyl acetate and $C_1$-$C_4$ branched or normal chain alcohol at refluxed temperature to form a solution;
b) cooling the solution to crystallize out 4-nitro tartranilic acid salt of (R)-isomer of 4-benzyl salbutamol of the formula (3):

Formula (3)

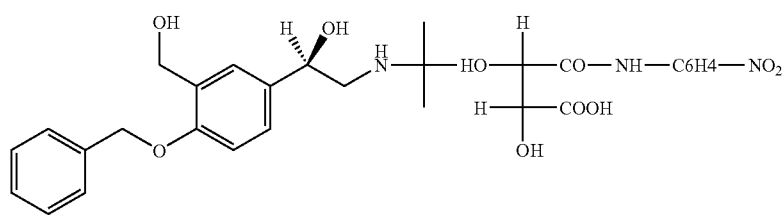

and isolating the compound of formula (3) by filtration to leave 4-nitro tartranilic acid salt of (S)-isomer of 4-benzyl salbutamol of the formula (7):

Formula (7)

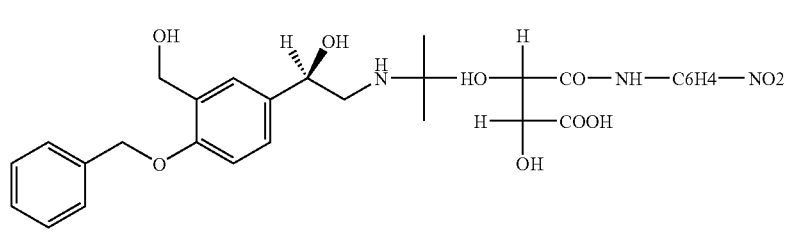

and traces of the compound of the formula (3) in the filtrate;
c) purifying the 4-nitro tartranilic acid salt of (R)-isomer of 4-benzyl salbutamol of the formula (3) by treating it with a binary solvent system comprising alkyl acetate and $C_1$ to $C_4$ branched or normal chain alcohol and isolating the compound of the formula (3) by filtration;
d) treating the 4-nitro tartranilic acid salt of (R)-isomer of 4-benzyl salbutamol of the formula (3) with 5 to 15% formic acid solution to form formic acid salt of (R)-isomer of 4-benzyl salbutamol of the formula (4):

Formula(4)

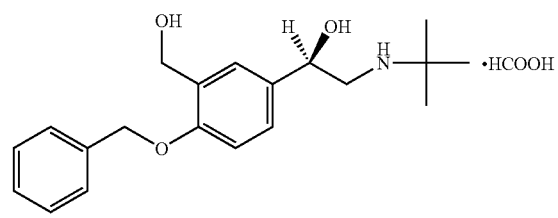

and liberate (+) 4-nitro tartranilic acid of the formula (2);
e) separating out the (+) 4-nitro tartranilic acid of the formula (2) by filtration;
f) cooling the filtrate containing formic acid salt of (R)-isomer of 4-benzyl salbutamol of the formula (4) to 5 to 10° C. followed by basifying the filtrate to pH 9 to 9.5 by adding a base such as ammonia to obtain enantiomeric pure (R)-isomer of 4-benzyl salbutamol of the formula (5):

Formula (5)

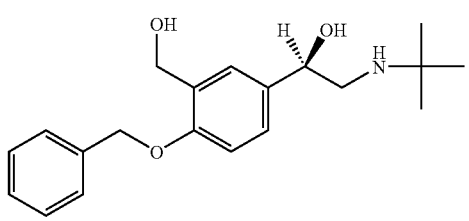

and isolating the (R)-isomer of the formula (5) by extracting it with methylene chloride followed by distilling out the solvent to obtain a residue, treating the residue with toluene at 80-85° C., cooling the solution to 0-5° C. to precipitate optically pure (R)-isomer of the formula (5) and filtering the optically pure (R)-isomer of formula (5);

g) debenzylating the (R)-isomer of the formula (5) to obtain optically pure (R) isomer of salbutamol of the formula (6);

Formula (6)

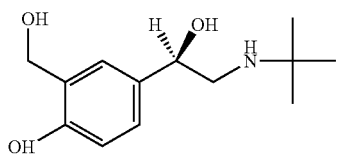

and h) optionally converting the optically pure (R)-isomer of salbutamol of the formula (6) into its hydrochloride or sulfate salt.

According to the invention the process also comprises racemizing 4-nitro tartranilic acid salt of (S)-isomer of 4-benzyl salbutamol of the formula (7):

Formula (7)

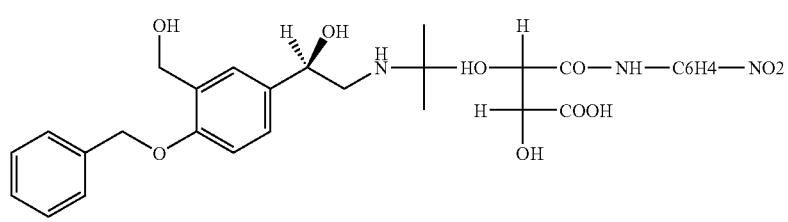

and traces of 4-nitro tartranilic acid salt of (R) isomer of 4-benzyl salbutamol of the formula (3) contained in the filtrate of the steps (a) and (b) by subjecting the filtrate to vacuum distillation to obtain a residue followed by treating the residue with 5 to 10% formic acid solution with stirring to obtain a gummy mass comprising formic acid salt of (S) isomer of 4-benzyl salbutamol of the formula (8):

Formula 8

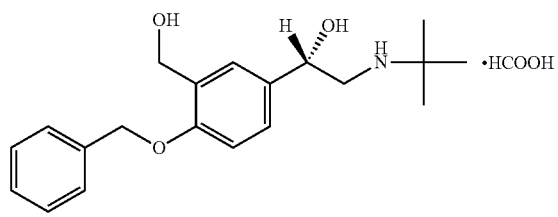

and formic acid salt of (R)-isomer of 4-benzyl salbutamol of the formula (4) and liberate (+) 4-nitro tartranilic acid of the formula (2);

separating the compound of the formula (2) by filtration;

basifying the filtrate to 9 to 9.5 pH by adding a base such as ammonia at 5 to 10° C. to obtain a mixture comprising (S)-isomer of 4-benzyl salbutamol of the formula (9):

(9)

Formula 9

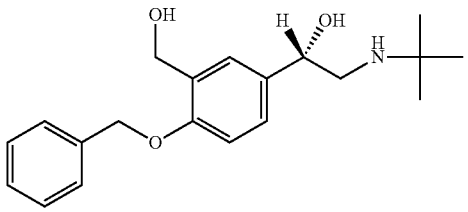

and traces of (R)-isomer of 4-benzyl salbutamol of the formula (4);

treating the above mixture with acetic anhydride at reflux temperature followed by distillation under vacuum to obtain a residue comprising a diacetate of (S)-isomer of 4-benzyl salbutamol of the formula (10):

Formula 10

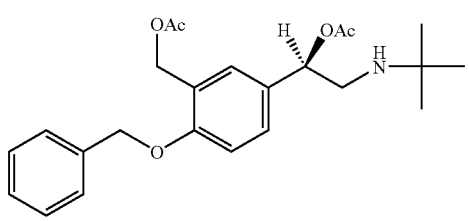

and traces of diacetate of (R)-isomer of 4-benzyl salbutamol of the formula (11):

Formula (11)

hydrolyzing the residue by treating it with base such as sodium hydroxide solution or potassium hydroxide solution at temperature in the range of 80 to 85° C., cooling the reaction mixture to precipitate a racemic mixture of 4-benzyl salbutamol and isolating the racemic mixture by filtration and drying the racemic mixture. The racemic mixture of 4-benzyl salbutamol isolated is recycled in the process to prepare optically pure (R)-isomer salbutamol.

Preferably, the alkyl acetate used in the binary system in step (a) or (b) is methyl acetate, ethyl acetate or iso-propyl acetate. Preferably, the $C_1$-$C_4$ branched or normal chain alcohol used in the binary system in step (a) or (b) is selected from a group consisting of methanol, ethanol, isopropanol, butanol or tert-Butanol, more preferably isopropanol. Preferably, the alkyl acetate and $C_1$-$C_4$ branched or normal chain alcohol used in the binary system in step (a) or (b) is in a ratio of 20:80 to 40:50 v/v. More preferably, the alkyl acetate and $C_1$-$C_4$ branched or normal chain alcohol used in the binary system in step (a) or (b) is in a ratio of 40:60 v/v. Preferably, the step (a) is carried out at a temperature in the range of 50 to 85° C. More preferably, the step (a) is carried out at a temperature of 75° C. Preferably, the dissolution step (a) is carried out at refluxed temperature for 40-55 hours. More preferably 45 hours. Preferably, the volume of binary solvent system used to purify 4-nitro tartranilic acid salt of (R)-isomer of 4-benzyl salbutamol of the formula (3) is 3 to 3.5 w/v.

Preferably, debenzylation of (R)-isomer of 4-benzyl salbutamol of the formula (5) is carried out by hydrogenating optically pure (R)-isomer 4-benzyl salbutamol of the formula (5) in the presence of Pd/C using methanol as solvent under 2-5 kg/cm pressure to obtain a optically pure (R) isomer of salbutamol of the formula (6).

The compound of the formula (6) is converted to the salt by treating it with the respective acid namely sulfuric or hydrochloric acid in known manner According to the process of the invention, the yield and optical purity of the (R)-isomer are about 45% and at least 99.9% ee respectively. Because of the use of 4-nitro tartranilic acid, the 4-nitro tartranilic acid salt of (S)-isomer of 4-benzyl salbutamol of the formula (7) is rendered highly soluble in the binary solvent system used in steps (a) and (b) whereas the (R)-isomer precipitated out. This facilitates easy and complete separation and recovery of the (R)-isomer. On using tartaric acid instead of 4-nitro tartranilic acid both the isomers remained in the solvent mixture and seeding was required to precipitate the (R)-isomer. The 4-nitro tartranilic acid salt of (S)-isomer of the formula (7) and traces of the (R)-isomer of the formula (3) in the filtrate of step (b) are also converted into racemic mixture of 4-benzyl salbutamol and reused in the process. Further the resolving agent of the formula (2) is also recovered and reused. Thus the process of the invention is efficient and cost-effective without sacrificing the optical purity of (R) isomer of salbutamol.

The following experimental examples are illustrative of the invention but not limitative of the scope thereof.

Example 1

700 gms of 4-benzyl salbutamol and 630 gms of 4-nitrotartranilic acid were added to 8400 ml. of isopropanol: ethyl acetate mixture (in 60:40 ratio) while stirring. The reaction mixture was heated to 75° C. with stirring for 44 hrs. The reaction mixture was cooled to crystallize 4-nitro tartranilic acid salt of (R)-isomer of 4-benzyl salbutamol and filtered the crystalline residue. The crystalline residue was stirred with 4964 ml. of isopropanol:ethyl acetate (60:40 ratio) at 70-75 degrees for 2 hours. The crystals of 4-nitro tartranilic acid salt of (R)-isomer of 4-benzyl salbutamol was filtered and dried at 60 degrees under vacuum. 160 mm. Both the filtrate obtained was combined which comprises essentially 4-nitro tartranilic acid salt of (S)-4-benzyl salbutamol and traces of 4-nitro tartranilic acid salt of (R)-4-benzyl salbutamol. The filtrate was used for racemization to recycle in the process.

Yield of 4-nitro tartranilic acid salt of (R)-isomer of 4-benzyl salbutamol 90%

100 gms of 4-nitro tartranilic acid salt of (R)-isomer of 4-benzyl salbutamol obtained was reacted with 1000 ml of 10% aqueous Formic acid while stirring for 1 hr. The reaction mixture was filtered to obtain resolving agent which was dried at 50-60° C. under vacuum 160 mm and can be reused. The filtrate comprising formic acid salt of (R)-isomer of 4-benzyl salbutamol was cooled to 10° C. The ammonia solution was added to adjust the pH of the filtrate to 9.5-10 while maintaining the temperature between 8-10° C. to precipitate (R)-isomer of 4-benzyl salbutamol. The precipitated (R)-isomer was extracted with 600 ml methylene chloride. The organic layer was separated and treated with 5 gm of activated charcoal for 30 minutes. The solution was filtered hot and the methylene chloride was distilled to obtain a residue comprising (R)-isomer of 4-benzyl salbutamol. The residue was heated in 250 ml toluene at 80° C. and maintained at same temperature for 15 minutes. The solution was then cooled to 0° C. and filtered. The (R)-isomer of 4-benzyl salbutamol was washed with 40 ml. toluene and then dried at 60° C. under vacuum 60 mm Yield of (R)-isomer of 4-benzyl salbutamol is 90%
Purity of (R)-isomer of 4-benzyl salbutamol is 99.92% ee
100 gm of (R)-isomer of 4-benzyl salbutamol was added to 2500 ml. of methanol while stirring. To this, 10 gm of 5% wet Pd/C was added and transferred to pressure vessel. The reaction mixture was hydrogenated under a pressure of 3-5 kg/cm2. The reaction was monitored on TLC. On completion, the reaction mixture was cooled and filtered. The filtrate was cooled to 0-5° C. and the pH of the filtrate was adjusted to 3.5-4.5 by adding 98% sulphuric acid to precipitate its sulfate salt while stirring for two hrs. The reaction mixture was filtered and washed with 50 ml methanol. R-Salbutamol Sulfate obtained was dried at 50-55° C. under 60 mm vacuum.

Yield of (R)-Salbutamol sulfate is 45%.
Purity of (R)-Salbutamol sulfate is 99.92% ee Example 2

The filtrate comprising (R)-isomer salbutamol obtained according to the Example 1 was cooled to 0-5° C. and the pH of the filtrate was adjusted to 3.5-4.5 by adding 11% hydrochloric acid to precipitate its chloride salt while stirring for two hrs. The reaction mixture was filtered and washed with 50 ml acetone. R-Salbutamol chloride obtained was dried at 50-55° C. under 60 mm vacuum.

Yield of (R)-Salbutamol chloride is 45%.
Purity of (R)-Salbutamol chloride is 99.92% ee Example 3

The filtrate comprising essentially 4-nitro tartranilic acid salt of (S)-4-benzyl salbutamol and traces of 4-nitro tartranilic acid salt of (R)-4-benzyl salbutamol obtained according to example 1 was distilled under vacuum to obtain gummy residue. The gummy residue was treated with 10% formic acid till it dissolves. The reaction mass was stirred for one hour. The reaction mass was filtered to recover the resolving agent, (+) 4-nitro tartranilic acid which used to recycle in the process. The filtrate was cooled to 10° C. and basified with ammonia while maintaining the temperature at 10° C. till pH becomes to 9.5-10. The free base was extracted with methylene chloride. The organic extract was further processed according to Example 1 to obtain obtained a mixture comprising essentially formic acid salt of (S)-isomer and traces of (R)-isomer of 4-benzyl salbutamol. The mixture (50 g) obtained was treated with 370 ml. acetic anhydride while stirring. The reaction mixture was heated to increase the temperature to 100-105° C. and refluxed for 2 hrs. The reaction mixture was subjected to vacuum distillation to obtain residue comprising diacetate salt of (R)-salbutamol and (S)-salbutamol. The residue was hydrolyzed by treating it with 417 ml of 10% sodium hydroxide solution at 80 to 85° C. The reaction mixture was stirring for 15 to 16 hours. The reaction was monitored on TLC. After completion of the reaction, the reaction mixture was filtered to obtain racemic mixture of 4-benzyl salbutamol. The racemic mixture was dried at 60° C.

Yield of the racemic mixture 4-benzyl salbutamol is 90%.

The invention claimed is:

1. A process for the preparation of optically pure R (−) salbutamol of the formula (6):

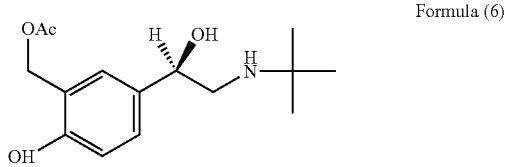

Formula (6)

and its pharmaceutically acceptable salts, the process comprising:

a) dissolving a racemic mixture of 4-benzyl salbutamol of the formula (1):

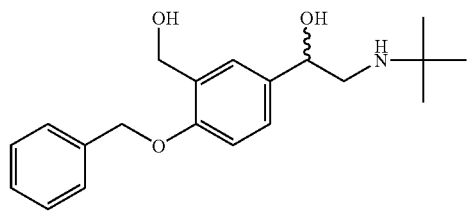

Formula (1)

and (+) 4-nitro tartranilic acid of the Formula (2):

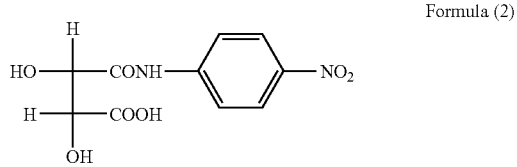

Formula (2)

in a binary solvent system comprising alkyl acetate and alcohol at refluxed temperature to form a solution;

b) cooling the solution to crystallize out 4-nitro tartranilic acid salt of (R)-isomer of 4-benzyl salbutamol of the formula (3):

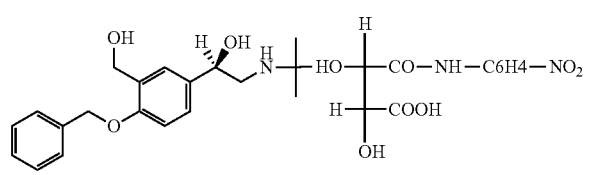

Formula (3)

and isolating the compound of formula (3) by filtration to leave 4-nitro tartranilic acid salt of (S)-isomer of 4-benzyl salbutamol of the formula (7):

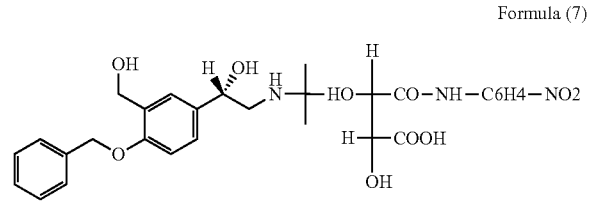

Formula (7)

and traces of the compound of the formula (3) in the filtrate;

c) purifying the 4-nitro tartranilic acid salt of (R)-isomer of 4-benzyl salbutamol of the formula (3) by treating it with a binary solvent system comprising alkyl acetate and alcohol and isolating the compound of the formula (3) by filtration;

d) treating 4-nitro tartranilic acid salt of (R)-isomer of 4-benzyl salbutamol of the formula (3) with 5 to 15 percent formic acid solution to obtain formic acid salt of (R)-isomer of 4-benzyl salbutamol of the formula (4):

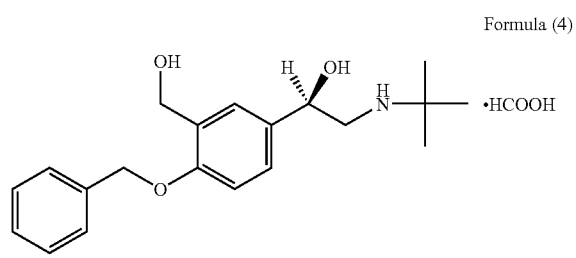

Formula (4)

and liberate (+) 4-nitro tartranilic acid of the formula (2);

e) separating out the (+) 4-nitro tartranilic acid of the formula (2) by filtration;

f) cooling the filtrate containing formic acid salt of (R)-isomer of 4-benzyl salbutamol of the formula (4) to 5 to 10 degree Celsius followed by basifying the filtrate to pH 9 to 9.5 by adding a base to obtain enantiomeric pure (R)-isomer of 4-benzyl salbutamol of the formula (5):

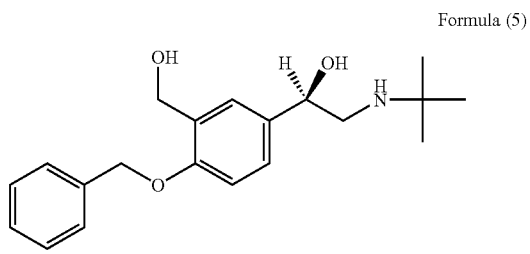

Formula (5)

and isolating the (R)-isomer by extracting it with methylene chloride followed by distilling out the solvent to obtain a residue, treating the residue with toluene at 80 to 85 degree Celsius, cooling the solution to 0 to 5 degree Celsius to precipitate optically pure (R)-isomer and filtering the optically pure (R)-isomer of formula (5); and g) debenzylating the (R)-isomer of the formula (5) to obtain optically pure (R) isomer of Salbutamol of the formula (6):

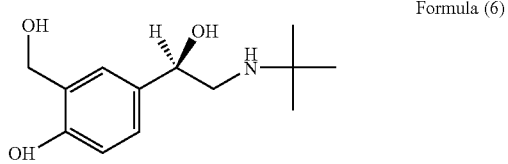

Formula (6)

2. The process as claimed in claim 1 further comprising:

racemizing 4-nitro tartranilic acid salt of (S)-isomer of 4-benzyl salbutamol of the formula (7):

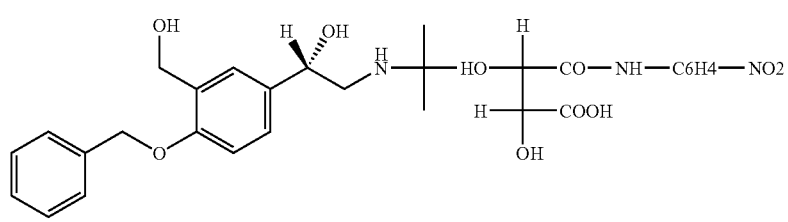

Formula (7)

and traces of 4-nitro tartranilic acid salt of (R) isomer of 4-benzyl salbutamol of the formula (3):

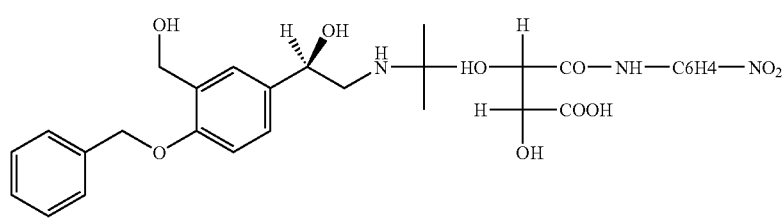

Formula (3)

contained in the filtrate of the steps (a) and (b) by subjecting the filtrate to vacuum distillation to obtain a residue followed by treating the residue with 5 to 10 percent formic acid solution to obtain a gummy mass comprising formic acid salt of (S) isomer of 4-benzyl salbutamol of the formula (8):

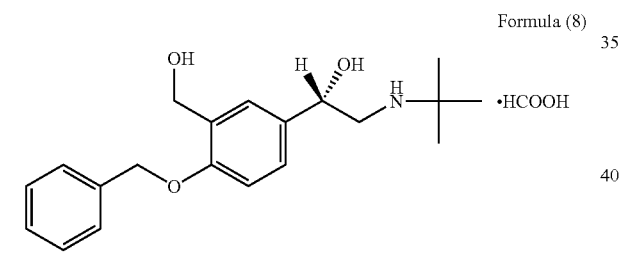

Formula (8)

and formic acid salt of (R)-isomer of 4-benzyl salbutamol of the formula (4) and liberate (+) 4-nitro tartranilic acid of the formula (2);
separating the compound of the formula (2) by filtration;
basifying the filtrate to 9 to 9.5 pH by adding a base at 5 to 10 degree Celsius to obtain a reaction mixture comprising (S)-isomer of 4-benzyl salbutamol of the formula (9):

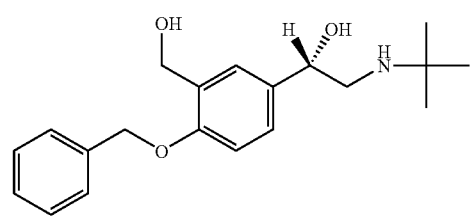

Formula (9)

and traces of (R)-isomer of 4-benzyl salbutamol of the formula (4);

treating the reaction mixture with acetic anhydride at reflux temperature followed by distillation under vacuum to obtain residue comprising diacetate salt of (S)-isomer of 4-benzyl salbutamol of the formula (10):

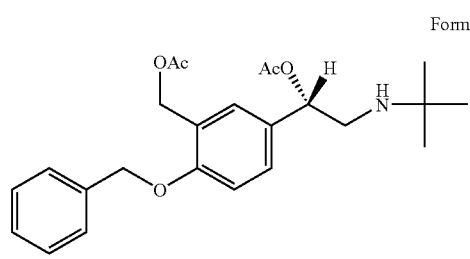

Formula (10)

and traces of diacetate salt of (R)-isomer of 4-benzyl salbutamol of the formula (11):

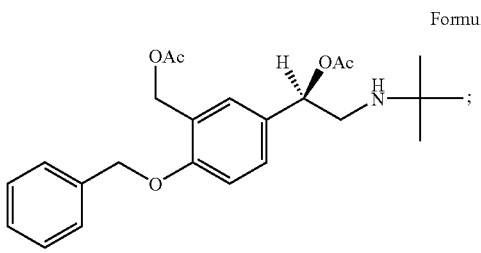

Formula (11)

hydrolyzing the residue by treating it with base at temperature in the range of 80 to 85 degree Celsius, cooling the reaction mixture to precipitate a racemic mixture of 4-benzyl salbutamol and isolating the recemic mixture by filtration.

3. The process as claimed in claim 1 wherein, the alkyl acetate used in the binary solvent system in step (a) or (b) or both is at least one selected from the group consisting of methyl acetate, ethyl acetate and iso-propyl acetate.

4. The process as claimed in claim 1 wherein, the alcohol used in the binary solvent system used in step (a) or (b) or both is at least one selected from the group consisting of methanol, ethanol, isopropanol, butanol and tert-Butanol.

5. The process as claimed in claim 1 wherein, the ratio of the alkyl acetate and the alcohol used in the binary solvent system used in step (a) or (b) or both is in the range of 20:80 to 40:50 v/v.

6. The process as claimed in claim 1 wherein, the ratio of the alkyl acetate and the alcohol used in the binary solvent system used in step (a) or (b) or both is about 40:60 v/v.

7. The process of claim 1 further comprising converting the optically pure (R)-isomer of salbutamol of the formula (6) into its hydrochloride salt.

8. The process of claim 1 further comprising converting the optically pure (R)-isomer of salbutamol of the formula (6) into its sulphate salt.

9. The process of claim 1 wherein the base added to basify the filtrate comprises ammonia.

10. The process of claim 2 wherein the base used for the hydrolyzing the residue comprises sodium hydroxide solution.

11. The process of claim 2 wherein the base used for the hydrolyzing the residue comprises potassium hydroxide solution.

12. The process of claim 2 wherein the base added to basify the filtrate comprises ammonia.

13. The process of claim 1 wherein the alcohol used in the binary solvent system used in step (a) or (b) or both is at least one selected from the group consisting of $C_1$ to $C_4$ branched alcohol and normal chain alcohol.

14. The process as claimed in claim 1 wherein, the 4-nitro tartranilic acid salt of (R)-isomer of 4-benzyl salbutamol of the formula (3) is purified with the binary solvent system using proportion 3 to 3.5 w/v.

* * * * *